US012721840B2

(12) United States Patent
Matsuda et al.

(10) Patent No.: US 12,721,840 B2
(45) Date of Patent: Sep. 1, 2026

(54) METHODS OF TREATING GLIOBLASTOMA MULTIFORME USING COMBINATION THERAPY

(71) Applicant: MediciNova, Inc., La Jolla, CA (US)

(72) Inventors: Kazuko Matsuda, La Jolla, CA (US); Michael Vogelbaum, Tampa, FL (US); Justin Lathia, Shaker Heights, OH (US)

(73) Assignee: MediciNova, Inc., La Jolla, CA (US)

( * ) Notice: Subject to any disclaimer, the term of this patent is extended or adjusted under 35 U.S.C. 154(b) by 529 days.

(21) Appl. No.: 17/947,560

(22) Filed: Sep. 19, 2022

(65) Prior Publication Data

US 2023/0090534 A1 Mar. 23, 2023

Related U.S. Application Data

(60) Provisional application No. 63/246,755, filed on Sep. 21, 2021.

(51) Int. Cl.

*A61K 31/437* (2006.01)
*A61K 9/00* (2006.01)
*A61K 31/47* (2006.01)
*A61K 31/495* (2006.01)
*A61P 35/00* (2006.01)

(52) U.S. Cl.

CPC .......... *A61K 31/437* (2013.01); *A61K 9/0019* (2013.01); *A61K 31/47* (2013.01); *A61K 31/495* (2013.01); *A61P 35/00* (2018.01)

(58) Field of Classification Search

CPC .... A61K 31/437; A61K 9/0019; A61K 31/47; A61K 31/495; A61P 35/00
See application file for complete search history.

(56) References Cited

U.S. PATENT DOCUMENTS

| | | | |
|---|---|---|---|
| 6,395,747 B1 | 5/2002 | Sakoda et al. | |
| 8,138,201 B2 | 3/2012 | Kalafer et al. | |
| 9,314,452 B2 | 4/2016 | Kalafer et al. | |
| 2006/0160843 A1 | 7/2006 | Johnson et al. | |
| 2016/0272707 A1* | 9/2016 | Levine | C07K 16/2803 |
| 2018/0177772 A1* | 6/2018 | Matsuda | A61K 31/4704 |

FOREIGN PATENT DOCUMENTS

| | | | |
|---|---|---|---|
| WO | WO-2018222949 A1 * | 12/2018 | A61K 47/46 |
| WO | WO 2019/157423 A1 | 8/2019 | |
| WO | WO 2020/028134 A1 | 2/2020 | |

OTHER PUBLICATIONS

Desai, Kunal, Anne Hubben, and Manmeet Ahluwalia. "The role of checkpoint inhibitors in glioblastoma." Targeted Oncology 14 (2019): 375-394. (Year: 2019).*

Passiglia, F., et al. "Primary and metastatic brain cancer genomics and emerging biomarkers for immunomodulatory cancer treatment." Seminars in Cancer Biology. vol. 52. Academic Press, 2018. (Year: 2018).*

Curigliano, et al., "Phase I/Ib Clinical Trial of Sabatolimab, an Anti-TIM-3 Antibody, Alone and in Combination with Spartalizumab, an Anti-PD-1 Antibody, in Advanced Solid tumors," *Clinical Cancer Research*, vol. 27, No. 13, pp. 3620-3629 (Jul. 2021).

Qie, et al., "Abstract LB-208: CD47 Blockade with Temozolomide can Enhance the Therapy in Glioblastoma," Cancer Res. 77 (13_ Supplement): LB-208 (Jul. 2017), 4 pages.

Huang, et al., "Immune Checkpoint in Glioblastoma: Promising and Challenging," *Frontiers in Pharmacology*, vol. 8, No. 242, (May 2017), 10 pages.

Ha, et al., "Ibudilast sensitizes glioblastoma to temozolomide by targeting Macrophage Migration Inhibitory Factor (MIF)," Scientific Reports, (2019) 10 pages.

McDonald, et al., "Ibudilast in Combination with Temozolomide Extends Survival in a Patient Xenograft Model," Jan. 1, 2017, 1 page.

International Search Report and Written Opinion issued in International Patent Application No. PCT/US2022/044003, dated Dec. 16, 2022.

Cho, et al., "Allosteric Inhibition of Macrophage Migration Inhibitory Factor Revealed by Ibudilast," *PNAS*, vol. 107, No. 25, pp. 11313-11318 (2010).

Gibson et al., "The Inhibitory Profile of Ibudilast Against the Human Phosphodiesterase Enzyme Family," European Journal of Pharmacology, vol. 538, pp. 39-42 (2006).

Sanftner et al., "Cross-species comparisons of the pharmacokinetics of ibudilast," Xenobiotica, vol. 39, No. 12, pp. 964-977 (Nov. 2009). [Abstract].

Obernolte, R., et al. (1993) "The cDNA of a human lymphocyte cyclic-AMP phosphodiesterase (PDE IV) reveals a multigene family" Gene 129: 239-247.

Rile et al., "Potentiation of Ibudilast Inhibition of Platelet Aggregation in the Presence of Endothelial Cells," Thrombosis Research, 102 239-246 (2001). [Abstract].

Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).

Suzumura et al., "Ibudilast suppresses TNF.alpha production by glial cells functioning mainly as type III phosphodiesterase inhibitor in NCS," Brain Research, 837:203-212 (1999).

Takuma et al., "Ibudilast attenuates actrocyte apoptsis via cyclic GMP signaling pathway in an in vitro reperfusion model," British Journal of Pharmacology, 133:841-848 (2001).

(Continued)

*Primary Examiner* — James H Altrum-Acevedo
*Assistant Examiner* — Justin Christopher Sanchez
(74) *Attorney, Agent, or Firm* — Foley & Lardner LLP

(57) ABSTRACT

Disclosed herein are compositions and methods for treating glioblastoma in a patient in need thereof by administration of ibudilast (3-isobutyryl-2-isopropylpyrazolo[1,5-a]pyridine) or a pharmaceutically acceptable salt thereof, and an immune checkpoint inhibitor.

11 Claims, 1 Drawing Sheet

(56) References Cited

OTHER PUBLICATIONS

Jeffery et al., "The preparation and characterization of poly(lactide-co-glycolide) microparticles. II. The Entrapment of a Model Protein Using a (water-in-oil)-in-water Emulsion Solvent Evaporation Technique," Pharm. Research, vol. 10, pp. 362-368 (1993).

Chen et al., "The Type IV Phosphodiesterase Inhibitor Rolipram Induces Expression Inhibitors p21Cip1 and p27Kip1, Resulting in Growth Inhibition, Increased Differentiation, and Subsequent Apoptosis of Malignant A-172 Glioma Cells," *Cancer Biol. Ther.*, 1(3), pp. 268-276 (2002).

Mizuno et al., "Neuroprotective role of phosphodiesterase inhibitor ibudilast on neuronal cell death induced by activated microglia," Neuropharmacology, vol. 46, pp. 404-411 (2004).

* cited by examiner

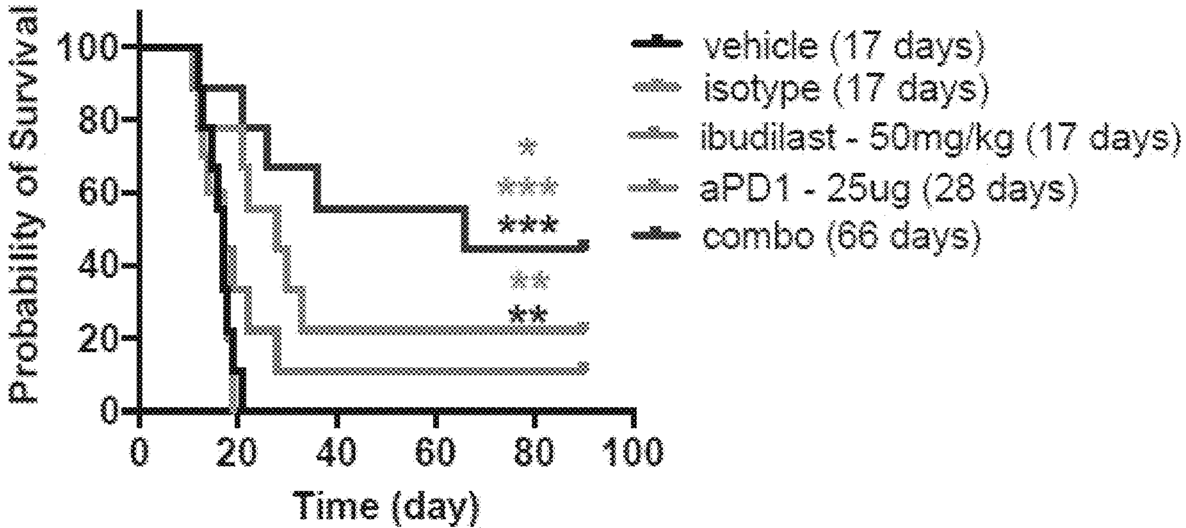
Probability of Survival
100
80
60
40
20
0
0
20
40
60
80
100
Time (day)
vehicle (17 days)
isotype (17 days)
ibudilast - 50mg/kg (17 days)
aPD1 - 25ug (28 days)
combo (66 days)
*
***
***
**
**

METHODS OF TREATING GLIOBLASTOMA MULTIFORME USING COMBINATION THERAPY

CROSS-REFERENCE TO RELATED APPLICATIONS

This application claims the benefit of priority to U.S. Provisional Patent Application No. 63/246,755, filed Sep. 21, 2021, and which is incorporated herein by reference in its entirety.

FIELD

The present disclosure relates generally to methods for treating glioblastoma multiforme (GBM), also known as glioblastoma, comprising administering a therapeutically effective amount of ibudilast (3-isobutyryl-2-isopropylpyrazolo[1,5-a]pyridine) and a therapeutically effective amount of an immune checkpoint inhibitor, such as an anti-PD-1 agent or an anti-PD-L1 agent.

BACKGROUND

The small molecule ibudilast (3-isobutyryl-2-isopropylpyrazolo[1,5-a]pyridine) is an inhibitor of macrophage inhibitory factor (MIF) (Cho et al PNAS-USA 2010 June 107: 11313-8) and selective inhibitor of cyclic nucleotide phosphodiesterases (PDEs) 3A, 4, 10A1 and 11A1 (Gibson et al., *Eur. J. Pharmacol.* 538: 39-42, 2006). Ibudilast distributes well to the CNS (Sanftner et al *Xenobiotica* 2009 39: 964-977) and at clinically-relevant plasma or CNS concentrations, ibudilast selectively inhibits macrophage migration inhibitory factor (MIF) and, secondarily, PDEs 3, 4, 10, and 11. Ibudilast also acts as a leukotriene D4 antagonist, an anti-inflammatory, a PAF antagonist, and a vasodilatory agent (Thompson Current Drug Reports). Ibudilast is thought to exert a neuroprotective role in the central nervous system of mammals, presumably via suppression of the activation of glial cells (Mizuno et al., Neuropharmacology 46: 404-411, 2004).

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

While the use of ibudilast for a number of varying indications has been reported to date, to the best of the Applicant's knowledge, its use in combination with an immune checkpoint inhibitor for treating glioblastoma multiforme (GBM) or recurring forms thereof or refractory forms thereof has heretofore remained largely unexplored.

SUMMARY

In one aspect, provided herein is a method of treating glioblastoma in a patient in need thereof, the method comprising administering to the patient a therapeutically effective amount of ibudilast or a pharmaceutically acceptable salt thereof, and a therapeutically effective amount of an immune checkpoint inhibitor. In some embodiments, the immune checkpoint inhibitor is an anti-PD-1 agent, an anti-PD-L1 agent, or an anti-CTLA-4 agent. In some embodiments, the immune checkpoint inhibitor is an anti-PD-1 agent. In some embodiments, the anti-PD-1 agent is an anti-PD-1 antibody. In some embodiments, the anti-PD-1 agent is selected from the group consisting of nivolumab, pembrolizumab, cemiplimab, spartalizumab, camrelizumab, sintilimab, tislelizumab, toripalimab, AMP-514, AMP-224, JTX-4014, dostarlimab, retifanlimab, and AUNP-12. In some embodiments, the immune checkpoint inhibitor is an anti-PD-L1 agent. In some embodiments, the anti-PD-L1 agent is an anti-PD-L1 antibody. In some embodiments, the anti-PD-L1 agent is selected from the group consisting of atezolizumab, avelumab, durvalumab, cosibelimab, CA-170, and BMS-986189. In some embodiments, the immune checkpoint inhibitor is an anti-CTLA-4 agent. In some embodiments, the anti-CTLA-4 agent is an anti-CTLA-4 antibody. In some embodiments, the anti-CTLA-4 agent is selected from the group consisting of ipilimumab and tremelimumab.

In some embodiments, the ibudilast or pharmaceutically acceptable salt thereof is administered for at least 3 months. In some embodiments, the ibudilast or pharmaceutically acceptable salt thereof is administered for at least six months. In some embodiments, the ibudilast or pharmaceutically acceptable salt thereof is administered for at least one year. In some embodiments, the ibudilast or pharmaceutically acceptable salt thereof is administered for at least two years.

In some embodiments, the ibudilast or pharmaceutically acceptable salt thereof is administered at least once daily. In some embodiments, the ibudilast or pharmaceutically acceptable salt thereof is administered orally.

In some embodiments, the therapeutically effective amount of ibudilast or a pharmaceutically acceptable salt thereof is at least 30 mg/day. In some embodiments, the therapeutically effective amount of ibudilast or a pharmaceutically acceptable salt thereof is from 0.1 mg to 720 mg per day. In some embodiments, the therapeutically effective amount of ibudilast or a pharmaceutically acceptable salt thereof is from 30 mg to 200 mg per day. In some embodiments, the therapeutically effective amount of ibudilast or a pharmaceutically acceptable salt thereof is 30 mg to 720 mg daily. In some embodiments, the therapeutically effective amount of ibudilast or a pharmaceutically acceptable salt thereof is 60 mg to 600 mg daily. In some embodiments, the therapeutically effective amount of ibudilast or a pharmaceutically acceptable salt thereof is 100 mg to 480 mg daily.

In some embodiments, the therapeutically effective amount of ibudilast or a pharmaceutically acceptable salt thereof is selected from the group consisting of 30 mg/day, 40 mg/day, 50 mg/day, 60 mg/day, 90 mg/day, 100 mg/day, 110 mg/day, 120 mg/day, 150 mg/day, 180 mg/day, 190 mg/day, 200 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

In some embodiments, the therapeutically effective amount is administered as a single dose or is divided into two, three, or four doses.

In some embodiments, the ibudilast or a pharmaceutically acceptable salt thereof and the at least one additional therapy are both administered continuously. In some embodiments, the ibudilast or a pharmaceutically acceptable salt thereof is administered continuously and the immune checkpoint inhibitor is administered periodically.

BRIEF DESCRIPTION OF THE DRAWING

FIGURE depicts results from a murine glioblastoma model (ibudilast treatment in a syngeneic mouse model (20,000 SB28 cells) synergized with anti-PD1), in which mice are treated with ibudilast, an anti-PD-1 antibody, or a combination of ibudilast and an anti-PD-1 antibody. Isotype serves as negative control for the anti-PD-1 antibody and vehicle serves as negative control for ibudilast. Treatment was initiated at day 7 post-engraftment with 3 intraperitoneal injections 3 days apart; n=10 mice/group (male); median survival provided for each group, *$p<0.05$, $p<0.01$, *$p<0.001$ as assessed by log-rank (colored stars indicate comparison to each control group).

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, Organic Chemistry (Allyn and Bacon, Inc., current addition); J. March, Advanced Organic Chemistry (McGraw Hill, current addition); *Remington: The Science and Practice of Pharmacy*, A. Gennaro, Ed., 20th Ed.; FDA's Orange Book, Goodman & Gilman *The Pharmacological Basis of Therapeutics*, J. Griffith Hardman, L. L. Limbird, A. Gilman, 11 th Ed., 2005, *The Merck Manual, 18th edition,* 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description and figure.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent includes ibudilast or a pharmaceutically acceptable salt thereof.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

"Glial cells" refer to various cells of the central nervous system also known as microglia, astrocytes, and oligodendrocytes.

The terms "subject", "individual" or "patient" are used interchangeably herein and refer to a vertebrate, preferably a mammal. Mammals include, but are not limited to, mice, rodents, rats, simians, humans, farm animals, dogs, cats, sport animals and pets.

The terms "pharmacologically effective amount" or "therapeutically effective amount" of a composition or agent, as provided herein, refer to a nontoxic but sufficient amount of the composition or agent to provide the desired response, such as a reduction or regression of clinical symptoms of glioblastoma. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about," particularly in reference to a given quantity, is meant to encompass deviations of plus or minus five percent.

As used herein, the term "astrocyte" refers to a specific cell type.

As used herein, the term "glioblastoma multiforme" or "glioblastoma" "or malignant glioma" are used interchangeably herein and refer to a brain tumor that arises from astrocytes. Glioblastoma, as used herein, includes recurrent glioblastoma.

As used herein, the term "treatment" or "treating" means any treatment of a disease or condition or associated disorder, in a patient, including:

- inhibiting the disease or condition, that is, arresting or suppressing the development of clinical symptoms, such as cachexia in cancer;
- relieving the disease or condition that is, causing the regression of clinical symptoms, e.g., increasing overall survival or reducing tumor burden;
- improving clinical outcome of the patient suffering from glioblastoma;

or any combination thereof.

The term "clinical outcome" refers to any clinical observation or measurement relating to a patient's reaction to a therapy. Non-limiting examples of improvement in clinical outcome include longer survival time, reduction in tumor size, non-growth in tumor size, and/or lack of exacerbation in neurological symptoms. Non-limiting examples of neurological symptoms include double vision, vomiting, loss of appetite, changes in mood and personality, changes in ability to think and learn, seizures, speech difficulty, and cognitive impairment. In addition, non-limiting examples of clinical outcomes include tumor response (TR), overall survival (OS), progression free survival (PFS), disease free survival, time to tumor recurrence (TTR), time to tumor progression (TTP), relative risk (RR), toxicity, or side effect. "Overall Survival" (OS) intends a prolongation in life expectancy as compared to naïve or untreated individuals or patients. "Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease. "Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer. "Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up. "Relative Risk" (RR), in statistics and mathematical epidemiology, refers to the risk of an event (or of developing a disease) relative to exposure. Relative risk is a ratio of the probability of the event occurring in the exposed group versus a non-exposed group.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

Ibudilast

The methods of the disclosure for the treatment of glioblastoma are based upon administration of ibudilast in combination with an immune checkpoint inhibitor. Ibudilast is a small molecule drug (molecular weight of 230.3) having the structure shown below.

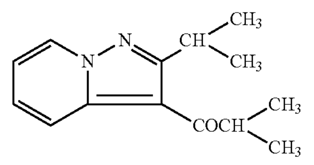

Ibudilast is also found under ChemBank ID 3227, CAS #50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine]; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is an inhibitor of the macrophage inhibitory factor (MIF). Ibudilast is also a selective inhibitor of cyclic nucleotide phosphodiesterases (PDEs) 3A, 4, 10A1 and 11A1 (Gibson et al., *Eur. J. Pharmacol.* 538: 39-42, 2006), and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca_2$+/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuro-active mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" *Gene* 129: 239-247; Rile, G., et al. (2001) "Potentiation of ibudilast inhibition of platelet aggregation in the presence of endothelial cells" *Thromb. Res.* 102: 239-246; Souness, J. E., et al. (1994) "Possible role of cyclic AMP phosphodiesterases in the actions of ibudilast on eosinophil thromboxane generation and airways smooth muscle tone" *Br. J. Pharmacol.* 111: 1081-1088; Suzumura, A., et al. (1999) "Ibudilast suppresses TNFα production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" *Br. J. Pharmacol.* 133: 841-848.

The use of rolipram (a PDE4 inhibitor) for treating glioblastoma has been suggested. See Chen et al., *Cancer Biol. Ther.* 2002, 1(3): 268-276. While rolipram showed positive results in cell assay studies and animal model studies, rolipram is not a great candidate for glioblastoma treatment in humans because of its poor penetration into the central nervous system (CNS). Ibudilast, on the other hand, exhibits good CNS penetration. (Sanftner et al Xenobiotica 2009 39: 964-977)

A reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Immune Checkpoint Inhibitors

The immune checkpoint inhibitors used in the methods of this disclosure include anti-PD-1 agents, anti-PD-L1 agents, and/or anti-CTLA-4 agents. In some embodiments, the immune checkpoint inhibitor is an anti-PD-1 agent. In some embodiments, the immune checkpoint inhibitor is an anti-PD-L1 agent. In some embodiments, the immune checkpoint inhibitor is an anti-CTLA-4 agent.

In some embodiments, the anti-PD-1 agent is an anti-PD-1 antibody. Non-limiting examples of the anti-PD-1 agent include nivolumab, pembrolizumab, pidilizumab, cemiplimab, spartalizumab, camrelizumab, sintilimab, tislelizumab, toripalimab, AMP-514, AMP-224, JTX-4014, dostarlimab, retifanlimab, and AUNP-12. In some embodiments, the anti-PD-1 agent is pembrolizumab.

In some embodiments, the anti-PD-L1 agent is an anti-PD-L1 antibody. Non-limiting examples of the anti-PD-L1 agent include atezolizumab, avelumab, envafolimab, durvalumab, cosibelimab, CA-170, and BMS-986189.

In some embodiments, the anti-CTLA-4 agent is an anti-CTLA-4 antibody. Non-limiting examples of the anti-CTLA-4 agent include ipilimumab and tremelimumab.

Methods of Treatment

As set forth above, the present disclosure is directed to a method of treating glioblastoma in a patient, including a human patient, in need thereof, the method comprising administering to the patient a therapeutically effective amount of ibudilast or a pharmaceutically acceptable salt thereof, and a therapeutically effective amount of an immune checkpoint inhibitor. In some embodiment, the method comprises administering to the patient a therapeutically effective amount of ibudilast or a pharmaceutically acceptable salt thereof, and a therapeutically effective amount of an anti-PD-1 agent. In some embodiment, the method comprises administering to the patient a therapeutically effective amount of ibudilast or a pharmaceutically acceptable salt thereof, and a therapeutically effective amount of an anti-PD-L1 agent. In some embodiment, the method comprises administering to the patient a therapeutically effective amount of ibudilast or a pharmaceutically acceptable salt thereof, and a therapeutically effective amount of an anti-CTLA-4 agent. Such administering is effective to decrease the amount of glioblastoma experienced by the patient, i.e., to result in a significant attenuation or even reversal of glioblastoma, as demonstrated in the accompanying Examples. Ibudilast or a pharmaceutically acceptable salt thereof is preferably administered at a daily dosage amount ranging from about 0.1 mg to 720 mg daily, from about 30 mg to 720 mg daily, from about 60 mg to 600 mg daily, or from about 100 mg to 480 mg daily.

The method of the disclosure may, in certain instances, comprise a step of selecting a patient experiencing glioblastoma prior to administering the combination of ibudilast and an immune checkpoint inhibitor (e.g., an anti-PD-1 agent, an anti-PD-L1 agent, or an anti-CTLA-4 agent) thereto.

In some embodiments, the ibudilast or a pharmaceutically acceptable salt thereof and the immune checkpoint inhibitor are both administered continuously. In some embodiments, the ibudilast or a pharmaceutically acceptable salt thereof is administered continuously and the immune checkpoint inhibitor is administered periodically.

Preferred methods of delivery of ibudilast-based therapeutic formulations for the treatment of glioblastoma include systemic and localized delivery. Such routes of administration include but are not limited to, oral, intra-arterial, intrathecal, intraspinal, intramuscular, intraperitoneal, intranasal, and inhalation routes.

More particularly, an ibudilast-based formulation of the present disclosure may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. In some embodiments, the ibudilast-based formulation is administered orally. In some embodiments, the ibudilast-based formulation is administered through an injection. The preferred route will, of course, vary with the condition and age of the recipient, the particular syndrome being treated, and the specific combination of drugs employed.

In some embodiments, the ibudilast or pharmaceutically acceptable salt thereof is administered orally. In some embodiments, the ibudilast or pharmaceutically acceptable salt thereof is administered through an injection.

The combination described herein may be administered as separate dosage forms. In instances in which the drugs comprising the therapeutic combination of the disclosure are administered as separate dosage forms and co-administration is required, ibudilast and the immune checkpoint inhibitor may be administered simultaneously, sequentially in any order, or separately.

Dosages: Ibudilast

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

A therapeutically effective amount of ibudilast or pharmaceutically acceptable salt thereof may range from a total daily dosage of about 0.1 mg/day to 720 mg/day, about 60-600 mg/day, or about 100-480 mg/day, or more preferably, in an amount between about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, the therapeutically effective amount of ibudilast or pharmaceutically acceptable salt thereof is from about 30-200 mg/day, administered as either a single dosage or as multiple dosages. In some embodiments, multiple dosages include two, three, or four doses per day.

Preferred dosage amounts of ibudilast include dosages greater than about 20 mg BID or TID. That is to say, a preferred dosage amount is greater than about 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day or more, or any value therebetween.

In some embodiments, the therapeutically effective amount of ibudilast or pharmaceutically acceptable salt thereof is at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, or at least 720 mg/day. In some embodiments, the therapeutically effective amount of ibudilast or pharmaceutically acceptable salt thereof is at least 60 mg/day. In some embodiments, the therapeutically effective amount of ibudilast or pharmaceutically acceptable salt thereof is at least 100 mg/day.

In some embodiments, the therapeutically effective amount of ibudilast or pharmaceutically acceptable salt thereof is about 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, or 720 mg/day, or any value therebetween.

Depending upon the dosage amount and precise condition to be treated, administration of ibudilast can be one, two, three, or four times daily for a time course of one day to several days, weeks, months, and even years, and may even be for the life of the patient. Illustrative dosing regimes will last a period of at least about a week, from about 1-4 weeks, from 1-3 months, from 1-6 months, from 1-52 weeks, from 1-24 months, or longer. In some embodiments, the ibudilast or the pharmaceutically acceptable salt thereof is administered for three months or less. In some embodiments, the ibudilast or the pharmaceutically acceptable salt thereof is administered for at least three months. In some embodiments, the ibudilast or the pharmaceutically acceptable salt thereof is administered for at least six months. In some embodiments, the ibudilast or the pharmaceutically acceptable salt thereof is administered for at least one year. In some embodiments, the ibudilast or the pharmaceutically acceptable salt thereof is administered for at least two years. In some embodiments, the ibudilast or the pharmaceutically acceptable salt thereof is administered for at least three years.

In some embodiments, the therapeutically effective amount of ibudilast or the pharmaceutically acceptable salt thereof is administered in a single dosage per day. In some embodiments, the therapeutically effective amount of ibudilast or the pharmaceutically acceptable salt thereof is administered in two dosages per day. In some embodiments, the therapeutically effective amount of ibudilast or the pharmaceutically acceptable salt thereof is administered in three dosages per day. In some embodiments, the therapeutically effective amount of ibudilast or the pharmaceutically acceptable salt thereof is administered in four dosages per day.

In some embodiments, the ibudilast or pharmaceutically acceptable salt thereof is administered at least once daily. In some embodiments, the ibudilast or pharmaceutically acceptable salt thereof is administered at least twice daily.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Dosing: Anti-PD-1 Agents

In some embodiments, the immune checkpoint inhibitor is nivolumab. Nivolumab may be daily administered at a minimum dose of 2 mg/kg/dose up to 600 mg/dose, for about 2 to about 12 weeks.

In some embodiments, the immune checkpoint inhibitor is pembrolizumab. Pembrolizumab may be daily administered at a minimum dose of 2 mg/kg/dose up to 600 mg/dose, for about 2 to about 12 weeks.

In some embodiments, the immune checkpoint inhibitor is cemiplimab. Cemiplimab may be daily administered at a minimum dose of 2 mg/kg/dose up to 600 mg/dose, for about 2 to about 12 weeks.

In some embodiments, the immune checkpoint inhibitor is spartalizumab. Spartalizumab may be daily administered at a minimum dose of 2 mg/kg/dose up to 600 mg/dose, for about 2 to about 12 weeks.

In some embodiments, the immune checkpoint inhibitor is camrelizumab. Camrelizumab may be daily administered at a minimum dose of 2 mg/kg/dose up to 600 mg/dose, for about 2 to about 12 weeks.

In some embodiments, the immune checkpoint inhibitor is sintilimab. Sintilimab may be daily administered at a minimum dose of 2 mg/kg/dose up to 600 mg/dose, for about 2 to about 12 weeks.

In some embodiments, the immune checkpoint inhibitor is tislelizumab. Tislelizumab may be daily administered at a minimum dose of 2 mg/kg/dose up to 600 mg/dose, for about 2 to about 12 weeks.

In some embodiments, the immune checkpoint inhibitor is toripalimab. Toripalimab may be daily administered at a minimum dose of 2 mg/kg/dose up to 600 mg/dose, for about 2 to about 12 weeks.

Dosing: Anti-PD-L1 Agents

In some embodiments, the immune checkpoint inhibitor is atezolizumab. Atezolizumab may be daily administered at a minimum dose of 5 mg/kg/dose up to 2000 mg/dose, for about 2 to about 12 weeks.

In some embodiments, the immune checkpoint inhibitor is avelumab. Avelumab may be daily administered at a minimum dose of 5 mg/kg/dose up to 2000 mg/dose, for about 2 to about 12 weeks.

In some embodiments, the immune checkpoint inhibitor is envafolimab. Envafolimab may be daily administered at a minimum dose of 5 mg/kg/dose up to 2000 mg/dose, for about 2 to about 12 weeks.

In some embodiments, the immune checkpoint inhibitor is durvalumab. Durvalumab may be daily administered at a minimum dose of 5 mg/kg/dose up to 2000 mg/dose, for about 2 to about 6 weeks.

Dosing: Anti-CTLA-4 Agents

In some embodiments, the immune checkpoint inhibitor is ipilumab. Ipilumab may be daily administered at a dose of 2 mg/kg/dose to 15 mg/kg/dose, for about 2 to about 12 weeks.

In some embodiments, the immune checkpoint inhibitor is tremelimumab. Tremelimumab may be daily administered at a dose of 2 mg/kg/dose to 15 mg/kg/dose, for about 2 to about 12 weeks.

Formulations

In addition to comprising ibudilast or a pharmaceutically acceptable salt thereof, a therapeutic formulation of the disclosure may optionally contain one or more excipients/carriers as described below.

Excipients/Carriers

In addition to ibudilast or a pharmaceutically acceptable salt thereof, the compositions of the disclosure for treating glioblastoma may further comprise one or more pharmaceutically acceptable excipients or carriers. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichioroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an ibudilast composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", 52. sup.nd ed., Medical Economics, Montvale, N.J. (1998), and Kibbe, A. H., Handbook of Pharmaceutical Excipients, 3. sup.rd Edition, American Pharmaceutical Association, Washington, D.C., 2000.

Sustained Delivery Formulations

Preferably, the compositions are formulated in order to improve stability and extend the half-life of ibudilast or the pharmaceutically acceptable salt thereof. For example, ibudilast or the pharmaceutically acceptable salt thereof may be delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast or the pharmaceutically acceptable salt thereof can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Delivery Forms

The ibudilast or pharmaceutically acceptable salt thereof compositions described herein encompass all types of formulations, and in particular, those that are suited for systemic or intrathecal administration. Oral dosage forms include tablets, lozenges, capsules, syrups, oral suspensions, emulsions, granules, and pellets. In some embodiments, the oral dosage form is a tablet. In some embodiments, the tablet is an extended release tablet. In some embodiments, the oral dosage form is a capsule. In some embodiments, the capsule is an extended release capsule.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast or pharmaceutically acceptable salt thereof composition of the disclosure is one suited for oral administration.

In turning now to oral delivery formulations, tablets can be made by compression or molding, optionally with one or more accessory ingredients or additives. Compressed tablets are prepared, for example, by compressing in a suitable tableting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tableting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate, and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravent® (Mallinkrodt), and the Acorn II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing at least one combination of the disclosure, accompanied by instructions for use.

For example, in instances in which each of the drugs themselves are administered as individual or separate dosage forms, the kit comprises ibudilast in addition to the immune checkpoint inhibitor making up the combination of the disclosure, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and an immune checkpoint inhibitor, the kit may be organized by any appropriate time period, such as by day. As an example, for Day 1, a representative kit may comprise unit dosages of each of ibudilast and the immune checkpoint inhibitor. If each of the drugs is to be administered twice daily, then the kit may contain, corresponding to Day 1, two rows of unit dosage forms of each of ibudilast and the immune checkpoint inhibitor, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister paks, dessicants, and the like.

Animal Models

The ability of the combination of ibudilast and an immune checkpoint inhibitor to treat glioblastoma can be evaluated by any of the standard glioblastoma models known in the art. Examples of such models are described in Animal Models of Neurological Disease: Neurodegenerative Diseases (Neuromethods) by Alan A. Boulton, Glen B. Baker, and Roger F. Butterworth (1992); Handbook of Laboratory Animal Science, Second Edition: Volumes I-III (Handbook of Laboratory Animal Science) by Jann Hau (Editor), Jr., Gerald L. Van Hoosier (Editor). (2004); Animal Models of Movement Disorders by Mark LeDoux (Editor), (2005); and Animal Models of Cognitive Impairment (Frontiers in Neuroscience) (2006) by Edward D. Levin (Editor), Jerry J. Buccafusco (Editor).

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1: Murine GBM Model

Mice bearing GBM orthotopic tumors were subjected to treatment with a PD-1 antibody in the presence or absence of ibudilast (or to ibudilast alone) and evaluated for their survival after the start of treatment. More particularly, ibudilast treatment (50 mg/kg) was performed in a syngeneic mouse model (20,000 SB28 cells) synergized with anti-PD1 (25 μg/dose). Treatment was initiated at day 7 post-engraftment with 3 intraperitoneal injections 3 days apart; n=10 mice/group (male).

Treatment with an anti-PD-1 antibody alone extended median survival from 17 to 28 days in this model, compared to control vehicle or non-specific antibody treatments. However, the addition of ibudilast to anti-PD1 antibody treatment further extended survival, to a median survival of 66 days (FIGURE). Ibudilast treatment alone did not impact median survival.

Example 2: Human Clinical Study

The study is an open label surgical "window-of-opportunity" in recurrent glioblastoma and a phase 1b study in newly-diagnosed glioblastoma.

Part 1

In Part 1, a safety run-in will be performed on 6 patients with recurrent glioblastoma to evaluate the toxicities and tolerability of the combination of ibudilast 100 mg orally daily and pembrolizumab 200 mg intravenously every 3 weeks. If the initial ibudilast dose of 60 mg daily is not tolerated, lower doses of 40 mg daily and 30 mg daily will be explored.

If the combination is tolerated, a surgical window-of-opportunity trial will be performed to evaluate the effect of the combination on the tumor immune response. Forty evaluable patients with recurrent glioblastoma requiring reoperation will be randomized to receive 2-3 weeks prior to surgery either Group 1: ibudilast alone (100 mg daily) (10 patients); Group 2: pembrolizumab alone 200 mg intravenously (10 patients); Group 3: the combination of ibudilast (100 mg daily) and pembrolizumab (200 mg) (10 patients); or Group 4: No treatment (control) (10 patients). At surgery, the tumor will be removed for analysis of the immune response.

Tumor tissue will be analyzed using next generation sequencing to quantify tumor infiltrating lymphocyte (TIL) density and T-cell receptor (TCR) repertoire and by immunohistochemistry. Blood will be collected at baseline, at the time of surgery, and at each scheduled follow-up visit during the postoperative period until progression for immunophenotyping of systemic immune cell subsets, MDSCs, and measurement of soluble immune cytokines.

After recovery from surgery, all patients will receive ibudilast 100 mg orally daily and pembrolizumab 200 mg every 3 weeks until tumor progression, development of unacceptable side effects, or a maximum of 2 years.

Patients will have MRI every 6 weeks. RANO18 and modified RANO19 criteria will be used.

Ultimately the efficacy of this combination may be greater in newly-diagnosed glioblastoma patients following debulking surgery and in combination with standard radiochemotherapy when the immune system may be more robust than at the time of recurrent disease. The safety and tolerability of the combination will be examined in newly-diagnosed glioblastoma in Part 2.

Part 2

In Part 2 the safety and efficacy and the recommended phase II dose of the combination of ibudilast and pembrolizumab with standard radiochemotherapy will be determined in patients with newly-diagnosed glioblastoma.

Eligible patients with undergo 6 weeks of radiotherapy (60 Gy) with concomitant temozolomide (75 $mg/m^2$ for 42 days), followed by a 4-week break, and the 6 cycles of temozolomide at 150-200 $mg/m^2/d \times 5$ every 28 days. Ibudilast 60 mg/day orally and pembrolizumab 200 mg intravenously every 3 weeks will be administered with the start radiochemotherapy until disease progression, development of unacceptable toxicity or for a maximum of 2 years. A 3+3 design will be used. Dose-limiting toxicities (DLT) will be determined during the first 10 weeks of treatment. If there are 0/3 or 1/6 DLTs at ibudilast 60 mg daily, the ibudilast dose will be increased to 100 mg daily for the next 3-6 patients. If this increased dose is tolerated, an additional 18 patients will be enrolled at this dose to confirm tolerability. If the initial ibudilast dose of 60 mg daily is not tolerated, lower doses of 40 mg daily and 30 mg daily will be explored.

Certain Embodiments

Embodiment 1. A method of treating glioblastoma in a patient in need thereof, the method comprising administering to the patient a therapeutically effective amount of ibudilast, or a pharmaceutically acceptable salt thereof, and a therapeutically effective amount of an immune checkpoint inhibitor.

Embodiment 2. The method of Embodiment 1, wherein the immune checkpoint inhibitor is an anti-PD-1 agent, an anti-PD-L1 agent, or an anti-CTLA-4 agent.

Embodiment 3. The method of Embodiment 2, wherein the immune checkpoint inhibitor is an anti-PD-1 agent.

Embodiment 4. The method of Embodiment 2 or Embodiment 3, wherein the anti-PD-1 agent is an anti-PD-1 antibody.

Embodiment 5. The method of Embodiment 2 or Embodiment 3, wherein the anti-PD-1 agent is selected from the group consisting of nivolumab, pembrolizumab, cemiplimab, spartalizumab, camrelizumab, sintilimab, tislelizumab, toripalimab, AMP-514, AMP-224, JTX-4014, dostarlimab, retifanlimab, and AUNP-12.

Embodiment 6. The method of Embodiment 2, wherein the immune checkpoint inhibitor is an anti-PD-L1 agent.

Embodiment 7. The method of Embodiment 2 or Embodiment 6, wherein the anti-PD-L1 agent is an anti-PD-L1 antibody.

Embodiment 8. The method of Embodiment 2 or Embodiment 6, wherein the anti-PD-L1 agent is selected from the group consisting of atezolizumab, avelumab, envafolimab, durvalumab, cosibelimab, CA-170, and BMS-986189.

Embodiment 9. The method of Embodiment 2, wherein the immune checkpoint inhibitor is an anti-CTLA-4 agent.

Embodiment 10. The method of Embodiment 2 or Embodiment 9, wherein the anti-CTLA-4 agent is an anti-CTLA-4 antibody.

Embodiment 11. The method of any one of Embodiments 2, 9, or 10, wherein the anti-CTLA-4 agent is selected from the group consisting of ipilimumab and tremelimumab.

Embodiment 12. The method of any one of Embodiments 1-11, wherein the ibudilast or pharmaceutically acceptable salt thereof is administered for at least 3 months.

Embodiment 13. The method of any one of Embodiments 1-11, wherein the ibudilast or pharmaceutically acceptable salt thereof is administered for at least six months.

Embodiment 14. The method of any one of Embodiments 1-11, wherein the ibudilast or pharmaceutically acceptable salt thereof is administered for at least one year.

Embodiment 15. The method of any one of Embodiments 1-11, wherein the ibudilast or pharmaceutically acceptable salt thereof is administered for at least two years.

Embodiment 16. The method of any one of Embodiments 1-15, wherein the ibudilast or pharmaceutically acceptable salt thereof is administered at least once daily.

Embodiment 17. The method of any one of Embodiments 1-16, wherein the ibudilast or pharmaceutically acceptable salt thereof is administered orally.

Embodiment 18. The method of any one of Embodiments 1-17, wherein the therapeutically effective amount of ibudilast or a pharmaceutically acceptable salt thereof is at least 30 mg/day.

Embodiment 19. The method of any one of Embodiments 1-17, wherein the therapeutically effective amount of ibudilast or a pharmaceutically acceptable salt thereof is from 0.1 mg to 720 mg per day.

Embodiment 20. The method of any one of Embodiments 1-17, wherein the therapeutically effective amount of ibudilast or a pharmaceutically acceptable salt thereof is from 30 mg to 200 mg per day Embodiment 21. The method of any one of Embodiments 1-17, wherein the therapeutically effective amount of ibudilast or a pharmaceutically acceptable salt thereof is 30 mg to 720 mg daily.

Embodiment 22. The method of any one of Embodiments 1-17, wherein the therapeutically effective amount of ibudilast or a pharmaceutically acceptable salt thereof is 60 mg to 600 mg daily.

Embodiment 23. The method of any one of Embodiments 1-17, wherein the therapeutically effective amount of ibudilast or a pharmaceutically acceptable salt thereof is 100 mg to 480 mg daily.

Embodiment 24. The method of any one of Embodiments 1-17, wherein the therapeutically effective amount of ibudilast or a pharmaceutically acceptable salt thereof is selected from the group consisting of 30 mg/day, 40 mg/day, 50 mg/day, 60 mg/day, 90 mg/day, 100 mg/day, 110 mg/day, 120 mg/day, 150 mg/day, 180 mg/day, 190 mg/day, 200 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

Embodiment 25. The method of any one of Embodiments 1-24, wherein the therapeutically effective amount of ibudilast or a pharmaceutically acceptable salt thereof is administered as a single dose or is divided into two, three, or four doses.

Embodiment 26. The method of any one of Embodiments 1-25, wherein the ibudilast or a pharmaceutically acceptable salt thereof and the immune checkpoint inhibitor are both administered continuously.

Embodiment 27. The method of any one of Embodiments 1-25, wherein the ibudilast or a pharmaceutically acceptable salt thereof is administered continuously and the immune checkpoint inhibitor is administered periodically.

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

Other embodiments are set forth in the following claims.

What is claimed is:

1. A method of treating glioblastoma in a patient in need thereof, the method comprising administering to the patient a therapeutically effective amount of ibudilast, or a pharmaceutically acceptable salt thereof, and a therapeutically effective amount of an anti-PD-1 antibody.

2. The method of claim 1, wherein the anti-PD-1 antibody is selected from the group consisting of nivolumab, pembrolizumab, cemiplimab, spartalizumab, camrelizumab, sintilimab, tislelizumab, toripalimab, AMP-514, JTX-4014, dostarlimab and retifanlimab.

3. The method of claim 1, wherein the ibudilast or pharmaceutically acceptable salt thereof is administered for at least 3 months.

4. The method of claim 1, wherein the ibudilast or pharmaceutically acceptable salt thereof is administered at least once daily.

5. The method of claim 1, wherein the ibudilast or pharmaceutically acceptable salt thereof is administered orally.

6. The method of claim 1, wherein the therapeutically effective amount of ibudilast or a pharmaceutically acceptable salt thereof is at least 30 mg/day.

7. The method of claim 1, wherein the therapeutically effective amount of ibudilast or a pharmaceutically acceptable salt thereof is from 0.1 mg to 720 mg per day.

8. The method of claim 1, wherein the therapeutically effective amount of ibudilast or a pharmaceutically acceptable salt thereof is selected from the group consisting of 30 mg/day, 40 mg/day, 50 mg/day, 60 mg/day, 90 mg/day, 100 mg/day, 110 mg/day, 120 mg/day, 150 mg/day, 180 mg/day, 190 mg/day, 200 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day.

9. The method of claim 1, wherein the therapeutically effective amount of ibudilast or a pharmaceutically acceptable salt thereof is administered as a single dose or is divided into two, three, or four doses.

10. The method of claim 1, wherein the ibudilast or a pharmaceutically acceptable salt thereof and the anti-PD-1 antibody are both administered continuously.

11. The method of claim 1, wherein the ibudilast or a pharmaceutically acceptable salt thereof is administered continuously, and the anti-PD-1 antibody is administered periodically.

* * * * *